US006274319B1

(12) United States Patent
Messier et al.

(10) Patent No.: US 6,274,319 B1
(45) Date of Patent: Aug. 14, 2001

(54) METHODS TO IDENTIFY EVOLUTIONARILY SIGNIFICANT CHANGES IN POLYNUCLEOTIDE AND POLYPEPTIDE SEQUENCES IN DOMESTICATED PLANTS AND ANIMALS

(76) Inventors: Walter Messier, 2418 Bowen St., Longmont, CO (US) 80501; James M. Sikela, 6046 S. Kingston Cir., Englewood, CO (US) 80111

( * ) Notice: Subject to any disclaimer, the term of this patent is extended or adjusted under 35 U.S.C. 154(b) by 0 days.

(21) Appl. No.: 09/368,810

(22) Filed: Aug. 5, 1999

Related U.S. Application Data

(63) Continuation-in-part of application No. 09/240,915, filed on Jan. 29, 1999.

(51) Int. Cl.[7] .................................................. C12Q 1/68
(52) U.S. Cl. ................................................. 435/6; 436/94
(58) Field of Search ................................. 435/6; 436/94

(56) References Cited

PUBLICATIONS

Raz et al., Mol. Gen. Genet. 233, 252–259, 1992.*
Yuhki et al., J. Immunol. 158, 2822–2833, 1997.*
Ann Gibbons, "Which of Our Genes Make Us Human?", Science Magazine, Sep. 4, 1998, 281: 1432–1434, downloaded from website www.sciencemag.org.
Li (1997) in Molecular Evolution, Sinauer Associates, Inc. Pub., Sunderland, MA, Table of Contents.
Nei (1987) in Molecular Evolutionary Genetics, Columbia University Press Pub., New York, NY, Table of Contents.
Yang (1998) Mol. Biol. Evol. 15:568–573.
Alter et al. (1984) Science 226:549–552.
Burger et al. (1994) J. Mol. Evol. 39:255–267.
Doebley et al. (1990) Proc. Natl. Acad. Sci. USA 87:9888–9892.
Dorweiler et al. (1993) Science 262:233–235.
Edwards et al. (1995) Molecular Ecology 4:719–729.
Endo et al. (1996) Mol. Biol. Evol. 13:685–690.
Fultz et al. (1986) Journal of Virology 58:116–124.
Goodman et al. (1990) J. Mol. Evol. 30:260–266.
Goodwin et al. (1996) Mol. Biol. Evol. 13:346.
Herbert et al. (1996) Mol. Biol. Evol. 13:1054–1057.
Hughes and Nei (1988) Nature 335:167–170.
Hughes (1997) Mol. Biol. Evol. 14: 1–5.
Jaeger et al. (1994) Immunogenetics 40:184–191.
Jenkins et al. (1995) Proc. R. Soc. Lond. 261:203–207.
Kreitman and Akashi (1995) Annu. Rev. Ecol. Syst. 26:403–422.
Lee et al. (1998) Aids Research and Human Retroviruses 14:1323–1328.
Lee and Vacquier (1992) Biol. Bull. 182:97–104.
Li et al. (1985) Mol. Biol. Evol. 2:150–174.
Li (1993) J. Mol. Evol. 36:96–99.
Lienert and Parham (1996) Immunol. Cell Biol. 74:349–356.
Lyn et al. (1995) Gene 152:241–245
Malcolm et al. (1990) Nature 345:86–89.
McDonald and Kreitman (1991) Nature 351:652–654.
Messier and Stewart (1994) Current Biology 4:911–913.
Messier and Stewart (1997) Nature 385:151–154.
Metz and Palumbi (1996) Mol. Biol. Evol. 13:397–406.
Nakashima et al. (1995) Proc. Natl. Acad. Sci. USA 92:5605–5609.
Nei and Hughes in Evolution at the Molecular Level, Sinauer Associates, Sunderland, MA, pp. 222–247 (1991).
Niewiesk and Bangham (1996) J. Mol. Evol. 42:452–458.
Novembre et al. (1997) Journal of Virology 71:4086–4091.
Parham and Ohta (1996) Science 272:67–74.
Paterson et al. (1995) Science 269:1714–1718.
Sharp (1997) Nature 385:111–112.
Swanson & Vacquier (1995) Proc. Natl. Acad. Sci. USA 92:4957–4961.
Swanson and Vacquier (1998) Science 281:710–712.
Turcich et al. (1996) Sex Plan Reprod. 9:65–74.
Wang et al. (1999) Nature 398:236–239.
Wettstein et al. (1996) Mol. Biol. Evol. 13: 56–66.
Whitfield et al. (1993) Nature 364:713–715.
Wolinsky et al. (1996) Science 272:537–542.
Wu et al. (1997) J. Mol. Evol. 44:477–491.
Zhou and Li (1996) Mol. Biol. Evol. 13:780–783.

* cited by examiner

Primary Examiner—Kenneth R. Horlick

(57) ABSTRACT

The present invention provides methods for identifying polynucleotide and polypeptide sequences which may be associated with commercially or aesthetically relevant traits in domesticated plants or animals. The methods employ comparison of homologous genes from the domesticated organism and its ancestor to identify evolutionarily significant changes. Sequences thus identified may be useful in enhancing commercially or aesthetically desirable traits in domesticated organisms.

34 Claims, No Drawings ent rate, and thus supports the existence of Darwinian molecular-level positive selection. For example, McDonald and Kreitman (1991) *Nature* 351:652–654, propose a statistical test of neutral protein evolution hypothesis based on comparison of the number of amino acid replacement substitutions to synonymous substitutions in the coding region of a locus. When they apply this test to the Adh locus of three Drosophila species, they conclude that it shows instead that the locus has undergone adaptive fixation of selectively advantageous mutations and that selective fixation of adaptive mutations may be a viable alternative to the clocklike accumulation of neutral mutations as an explanation for most protein evolution. Jenkins et al. (1995) *Proc. R. Soc. Lond.* B 261:203–207 use the McDonald & Kreitman test to investigate whether adaptive evolution is occurring in sequences controlling transcription (non-coding sequences).

METHODS TO IDENTIFY EVOLUTIONARILY SIGNIFICANT CHANGES IN POLYNUCLEOTIDE AND POLYPEPTIDE SEQUENCES IN DOMESTICATED PLANTS AND ANIMALS

CROSS-REFERENCE TO RELATED APPLICATIONS

This application is a continuation-in-part of U.S. application Ser. No. 09/240,915, filed Jan. 29, 1999, which is incorporated herein in its entirety by reference.

TECHNICAL FIELD

This invention relates to using molecular and evolutionary techniques to identify polynucleotide and polypeptide sequences corresponding to commercially or aesthetically relevant traits in domesticated plants and animals.

BACKGROUND ART

Humans have bred plants and animals for thousands of years, selecting for certain commercially valuable and/or aesthetic traits. Domesticated plants differ from their wild ancestors in such traits as yield, short day length flowering, protein and/or oil content, ease of harvest, taste, disease resistance and drought resistance. Domesticated animals differ from their wild ancestors in such traits as fat and/or protein content, milk production, docility, fecundity and time to maturity. At the present time, most genes underlying the above differences are not known, nor, as importantly, are the specific changes that have evolved in these genes to provide these capabilities. Understanding the basis of these differences between domesticated plants and animals and their wild ancestors will provide useful information for maintaining and enhancing those traits. In the case crop plants, identification of the specific genes that control for desired traits will allow direct and rapid improvement in a manner not previously possible.

Although comparison of homologous genes or proteins between domesticated species and their wild ancestors may provide useful information with respect to conserved molecular sequences and functional features, this approach is of limited use in identifying genes whose sequences have changed due to human imposed selective pressures. With the advent of sophisticated algorithms and analytical methods, much more information can be teased out of DNA sequence changes with regard to which genes have been positively selected. The most powerful of these methods, "$K_A/K_S$," involves pairwise comparisons between aligned protein-coding nucleotide sequences of the ratios of $$\frac{\text{nonsynonymous nucleotide substitutions per nonsynonymous site } (K_A)}{\text{synonymous substitutions per synonymous site } (K_S)}$$

(where nonsynonymous means substitutions that change the encoded amino acid and synonymous means substitutions that do not change the encoded amino acid). "$K_A/K_S$-type methods" includes this and similar methods.

These methods have already been used to demonstrate the occurrence of Darwinian (i.e., natural) molecular-level positive selection, resulting in amino acid differences in homologous proteins. Several groups have used such methods to document that a particular protein has evolved more rapidly than the neutral substitution rate, and thus supports the existence of Darwinian molecular-level positive selection.

Nakashima et al. (1995) *Proc. Natl. Acad. Sci USA* 92:5606–5609, use the method of Miyata and Yasunaga to perform pairwise comparisons of the nucleotide sequences of ten PLA2 isozyme genes from two snake species; this method involves comparing the number of nucleotide substitutions per site for the noncoding regions including introns ($K_N$) and the $K_A$ and $K_S$. They conclude that the protein coding regions have been evolving at much higher rates than the noncoding regions including introns. The highly accelerated substitution rate is responsible for Darwinian molecular-level evolution of PLA2 isozyme genes to produce new physiological activities that must have provided strong selective advantage for catching prey or for defense against predators. Endo et al. (1996) *Mol. Biol. Evol.* 13(5):685–690 use the method of Nei and Gojobori, wherein $d_N$ is the number of nonsynonymous substitutions and $d_S$ is the number of synonymous substitutions, for the purpose of identifying candidate genes on which positive natural selection operates. Metz and Palumbi (1996) *Mol. Biol. Evol.* 13(2):397–406 use the McDonald & Kreitman (supra) test as well as a method attributed to Nei and Gojobori, Nei and Jin, and Kumar, Tamura, and Nei; examining the average proportions of $P_n$, the replacement substitutions per replacement site, and $P_s$, the silent substitutions per silent site, to look for evidence of positive selection on binding genes in sea urchins to investigate whether they have rapidly evolved as a prelude to species formation. Goodwin et al. (1996) *Mol. Biol. Evol.* 13(2):346–358 uses similar methods to examine the evolution of a particular murine gene family and conclude that the methods provide important fundamental insights into how selection drives genetic divergence in an experimentally manipulatable system. Edwards et al. (1995) use degenerate primers to pull out MHC loci from various species of birds and an alligator species, which are then analyzed by the Nei and Gojobori methods ($d_N$:$d_S$ ratios) to extend MHC studies to nomnammalian vertebrates. Whitfield et al. (1993) *Nature* 364:713–715 use $K_A/K_S$ analysis to look for directional selection in the regions flanking a conserved region in the SRY gene (that determines male sex). They suggest that the rapid evolution of SRY could be a significant cause of reproductive isolation, leading to new species. Wettsetin et al. (1996) *Mol. Biol. Evol.* 13(1):56–66 apply the MEGA program of Kumar, Tamura and Nei and phylogenetic analysis to investigate the diversification of MHC class I genes in squirrels and related rodents. Parham and Ohta (1996) *Science* 272:67–74 state that a population biology approach, including tests for selection as well as for gene conversion and neutral drift are required to analyze the generation and maintenance of human MHC class I polymorphism. Hughes (1997) *Mol. Biol. Evol.* 14(1):1–5 compared over one hundred orthologous immunoglobulin C2 domains between human and rodent, using the method of Nei and Gojobori ($d_N$:$d_S$ ratios) to test the hypothesis that proteins expressed in cells of the vertebrate immune system evolve unusually rapidly. Swanson and Vacquier (1998) *Science* 281:710–712 use $d_N$:$d_S$ ratios to demonstrate concerted evolution between the lysin and the egg receptor for lysin and discuss the role of such concerted evolution in forming new species (speciation). Messier and Stewart (1997) *Nature* 385:151–154, used $K_A/K_S$ to demonstrate positive selection in primate lysozymes.

The genetic changes associated with domestication have been most extensively investigated in maize (corn) (Dorweiler (1993) *Science* 262:232–235). For maize, (*Zea* ssp. *mays mays*), a smaller number of single-gene changes apparently accounts for all the differences between our present domesticated maize plant and its wild ancestor, teosinte (*Zea mays* ssp *paruiglumis*) (Dorweiler, 1993). QTL (quantitative trait locus) analysis has demonstrated (Doebley (1990) *PNAS USA* 87:9888–9892) that no more than fifteen genes control traits of interest in maize and explain the profound difference in morphology between maize and teosinte (Wang (1999) *Nature* 398:236–239).

Importantly, a similarly small number of genes may control traits of interest in other grass-derived crop plants, including rice, wheat, millet and sorghum (Paterson (1995) *Science* 269:1714–1718). In fact, for most of these relevant genes in maize, the homologous gene may control similar traits in other grass-derived crop plants (Paterson, 1995). Thus, identification of these genes in maize would facilitate identification of homologous genes in rice, wheat, millet and sorghum.

As can be seen from the papers cited above, analytical methods of molecular evolution to identify rapidly evolving genes ($K_A/K_S$-type methods) can be applied to achieve many different purposes, most commonly to confirm the existence of Darwinian molecular-level positive selection, but also to assess the frequency of Darwinian molecular-level positive selection, to understand phylogenetic relationships, to elucidate mechanisms by which new species are formed, or to establish single or multiple origin for specific gene polymorphisms. What is clear is from the papers cited above and others in the literature is that none of the authors applied $K_A/K_S$-type methods to identify evolutionary changes in domesticated plants and animals brought about by artificial selective pressures. While Turcich et al. (1996) *Sexual Plant Reproduction* 9:65–74, describes the use of $K_S$ analysis on plant genes, it is believed that no one has used $K_A/K_S$ type analysis as a systematic tool for identifying in domesticated plants and animals those genes that contain evolutionarily significant sequence changes that can be exploited in the development, maintenance or enhancement of desirable commercial or aesthetic traits.

The identification in domesticated species of genes that have evolved to confer unique, enhanced or altered functions compared to homologous ancestral genes could be used to develop agents to modulate these functions. The identification of the underlying domesticated species genes and the specific nucleotide changes that have evolved, and the further characterization of the physical and biochemical changes in the proteins encoded by these evolved genes, could provide valuable information on the mechanisms underlying the desired trait. This valuable information could be applied to developing agents that further enhance the function of the target proteins. Alternatively, further engineering of the responsible genes could modify or augment the desired trait. Additionally, the identified genes may be found to play a role in controlling traits of interest in other domesticated plants. A similar process can identify genes for traits of interest in domestic animals.

All references cited herein are hereby incorporated by reference in their entirety.

DISCLOSURE OF THE INVENTION

The present invention provides methods for identifying polynucleotide and polypeptide sequences having evolutionarily significant changes, which are associated with commercial or aesthetic traits in domesticated organisms including plants and animals. The invention uses comparative genomics to identify specific gene changes which may be associated with, and thus responsible for, structural, biochemical or physiological conditions, such as commercially or aesthetically relevant traits, and using the information obtained from these traits to develop domesticated organisms with enhanced traits of interest.

In one preferred embodiment, a polynucleotide or polypeptide of a domesticated plant or animal has undergone artificial selection that resulted in an evolutionarily significant change present in the domesticated species that is not present in the wild ancestor. One example of this embodiment is that the polynucleotide or polypeptide may be associated with enhanced crop yield as compared to the ancestor. Other examples include short day length flowering (i.e., flowering only if the daily period of light is shorter than some critical length), protein content, oil content, ease of harvest, taste, drought resistance and disease resistance. The present invention can thus be useful in gaining insight into the molecular mechanisms that underlie functions or traits in domesticated organisms. This information can be useful in designing the polynucleotide so as to further enhance the function or trait. For example, a polynucleotide determined to be responsible for improved crop yield could be subjected to random or directed mutagenesis, followed by testing of the mutant genes to identify those which further enhance the trait.

Accordingly, in one aspect, methods are provided for identifying a polynucleotide sequence encoding a polypeptide of a domesticated organism (e.g., a plant or animal), wherein the polypeptide may be associated with a commercially or aesthetically relevant trait that is unique, enhanced or altered in the domesticated organism as compared to the wild ancestor of the domesticated organism, comprising the steps of: a) comparing protein-coding nucleotide sequences of said domesticated organism to protein-coding nucleotide sequences of said wild ancestor; and b) selecting a polynucleotide sequence in the domesticated organism that contains a nucleotide change as compared to a corresponding sequence in the wild ancestor, wherein said change is evolutionarily significant.

In another aspect of the invention, methods are provided for identifying an evolutionary significant change in a protein-coding nucleotide sequence of a domesticated organism (e.g., a plant or animal), comprising the steps of: a) comparing protein-coding nucleotide sequences of the domesticated organism to corresponding sequences of a wild ancestor of the domesticated organism; and b) selecting a polynucleotide sequence in said domesticated organism that contains a nucleotide change as compared to the corresponding sequence of the wild ancestor, wherein the change is evolutionarily significant.

In some embodiments, the nucleotide change identified by any of the methods described herein is a non-synonymous substitution. In some embodiments, the evolutionary significance of the nucleotide change is determined according to the non-synonymous substitution rate ($K_A$) of the nucleotide sequence. In some embodiments, the evolutionarily significant changes are assessed by determining the $K_A/K_S$ ratio between the domesticated organism polynucleotide and the corresponding ancestral polynucleotide. Preferably the ratio is at least about 0.75, or with increasing preference, the ratio is at least about 1.25, 1.50 and 2.00.

In another aspect, the invention provides a method of identifying an agent which may modulate the relevant trait in the domesticated organism, said method comprising contacting at least one candidate agent with a cell, model system or transgenic plant or animal that expresses the polynucleotide sequence having the evolutionarily significant change, wherein the agent is identified by its ability to modulate function of the polypeptide.

Also provided is a method for large scale sequence comparison between protein-coding nucleotide sequences of a domesticated organism and protein-coding sequences from a wild ancestor, said method comprising: a) aligning the domesticated organism sequences with corresponding sequences from the wild ancestor according to sequence homology; and b) identifying any nucleotide changes within the domesticated organism's sequences as compared to the homologous sequences from the wild ancestor primate.

In another aspect, the subject invention provides a method for correlating an evolutionarily significant nucleotide change to a commercially or aesthetically relevant trait that is unique, enhanced or altered in a domesticated organism, comprising: a) identifying a nucleotide sequence having an evolutionarily significant change according to the methods described herein; and b) analyzing the functional effect of the presence or absence of the identified sequence in the domesticated organism or in a model system.

The domesticated plants used in the subject methods can be corn, rice, tomatoes, potatoes or any domesticated plant for which the wild ancestor is extant and known. For example, the ancestor of corn is teosinte; ancestors of wheat are *Triticum monococcum, T speltoides* and *Aegilops tauschii*; and ancestors of rice are *Oryza nivora* and *O. rufipogon*. The relevant trait can be any commercially or aesthetically relevant trait such as yield, short day length flowering, protein content, oil content, drought resistance, taste, ease of harvest or disease resistance.

The domesticated animals used in the subject methods can be any domesticated animal for which an ancestor is available including pigs, cattle, horses, dogs and cats. For example, an ancestor of the horse is Pryzewalskii's Horse; and ancestors of cattle include some Indian breeds. The relevant trait could, for example, be fat content, protein content, milk production, time to maturity, fecundity, docility or disease resistance and disease susceptibility.

DETAILED DESCRIPTION OF THE INVENTION

The present invention utilizes comparative genomics to identify specific gene changes which are associated with, and thus may contribute to or be responsible for, commercially or aesthetically relevant traits in domesticated organisms (e.g., plants and animals).

In a preferred embodiment, the methods described herein can be applied to identify the genes that control traits of interest in agriculturally important domesticated plants. Humans have bred domesticated plants for several thousand years without knowledge of the genes that control these traits. Knowledge of the specific genetic mechanisms involved would allow much more rapid and direct intervention at the molecular level to create plants with desirable or enhanced traits.

Humans, through artificial selection, have provided intense selection pressures on crop plants. This pressure is reflected in evolutionarily significant changes between homologous genes of domesticated organisms and their wild ancestors. It has been found that only a few genes, e.g., 10–15 per species, control traits of commercial interest in domesticated crop plants. These few genes have been exceedingly difficult to identify through standard methods of plant molecular biology. The $K_A/K_S$ and related analyses described herein can identify the genes controlling traits of interest if those genes have undergone changes in the protein-coding region.

For any crop plant of interest, cDNA libraries can be constructed from the domesticated species or subspecies and its wild ancestor. As is described in U.S. Ser. No. 09/240, 915, filed Jan. 29, 1999, the cDNA libraries of each are "BLASTed" against each other to identify homologous polynucleotides. Alternatively, the skilled artisan can access commercially and/or publicly available genomic or cDNA databases, rather than constructing cDNA libraries. Next, a $K_A/K_S$ or related analysis is conducted to identify selected genes that have rapidly evolved under selective pressure. These genes are then evaluated using standard molecular and transgenic plant methods to determine if they play a role in the traits of commercial or aesthetic interest. The genes of interest are then manipulated by, e.g., random or site-directed mutagenesis, to develop new, improved varieties, subspecies, strains or cultivars.

Similarly, the methods described herein can be applied to domesticated animals including pigs, cattle, horses, dogs, cats and other domesticated animals for which a wild ancestor is available. Cattle and horses, especially, represent important commercial interests. As with plants, humans have bred animals for thousands of years, and those intense selection pressures will be reflected in elevated $K_A/K_S$ rates for rapidly evolved genes of interest. Again, to identify homologous polynucleotides, constructed cDNA libraries of domesticated animals and their wild ancestors can be BLASTed against each other, and/or available public or private genomic or cDNA databases can be accessed. For homologous sequences, $K_A/K_S$ or related analyses can be conducted, which will identify the polynucleotides that have rapidly evolved under the artificial selective pressure. These genes are then evaluated using standard molecular and transgenic animal methods to determine if they play a role in the traits of commercial or aesthetic interest. Those genes can then be manipulated to develop new, improved animal varieties or subspecies.

The practice of the present invention employs, unless otherwise indicated, conventional techniques of molecular biology, genetics and molecular evolution, which are within the skill of the art. Such techniques are explained fully in the literature, such as: "Molecular Cloning: A Laboratory Manual", second edition (Sambrook et al., 1989); "Oligonucleotide Synthesis" (M. J. Gait, ed., 1984); "Current Protocols in Molecular Biology" (F. M. Ausubel et al., eds., 1987); "PCR: The Polymerase Chain Reaction", (Mullis et al., eds., 1994); "Molecular Evolution", (Li, 1997).

Definitions

As used herein, a "polynucleotide" refers to a polymeric form of nucleotides of any length, either ribonucleotides or deoxyribonucleotides, or analogs thereof. This term refers to the primary structure of the molecule, and thus includes double- and single-stranded DNA, as well as double- and single-stranded RNA. It also includes modified polynucleotides such as methylated and/or capped polynucleotides. The terms "polynucleotide" and "nucleotide sequence" are used interchangeably.

As used herein, a "gene" refers to a polynucleotide or portion of a polynucleotide comprising a sequence that encodes a protein. It is well understood in the art that a gene also comprises non-coding sequences, such as 5' and 3' flanking sequences (such as promoters, enhancers, repressors, and other regulatory sequences) as well as introns.

The terms "polypeptide," "peptide," and "protein" are used interchangeably herein to refer to polymers of amino acids of any length. These terms also include proteins that are post-translationally modified through reactions that include glycosylation, acetylation and phosphorylation.

The term "domesticated organism" refers to an individual living organism or population of same, a species, subspecies, variety, cultivar or strain, that has been subjected to artificial selection pressure and developed a commercially or aesthetically relevant trait. In some preferred embodiments, the domesticated organism is a plant selected from the group consisting of corn, wheat, rice, sorghum, tomato or potato, or any other domesticated plant of commercial interest, where an ancestor is known. In other preferred embodiments, the domesticated organism is an animal selected from the group consisting of cattle, horses, pigs, cats and dogs. A domesticated organism and its ancestor may be related as different species, subspecies, varieties, cultivars or strains or any combination thereof.

The term "wild ancestor" or "ancestor" means a forerunner or predecessor organism, species, subspecies, variety, cultivar or strain from which a domesticated organism, species, subspecies, variety, cultivar or strain has evolved. A domesticated organism can have one or more than one ancestor. Typically, domesticated plants can have one or a plurality of ancestors, while domesticated animals usually have only a single ancestor.

The term "commercially or aesthetically relevant trait" is used herein to refer to traits that exist in domesticated organisms such as plants or animals whose analysis could provide information (e.g., physical or biochemical data) relevant to the development of agents that can modulate the polypeptide responsible for the trait. The commercially or aesthetically relevant trait can be unique, enhanced or altered relative to the ancestor. By "altered," it is meant that the relevant trait differs qualitatively or quantitatively from traits observed in the ancestor.

The term "$K_A/K_S$-type methods" means methods that evaluate differences, frequently (but not always) shown as a ratio, between the number of nonsynonymous substitutions and synonymous substitutions in homologous genes (including the more rigorous methods that determine non-synonymous and synonymous sites). These methods are designated using several systems of nomenclature, including but not limited to $K_A/K_S$, $d_N/d_S$, $D_N/D_S$.

The terms "evolutionarily significant change" and "adaptive evolutionary change" refer to one or more nucleotide or peptide sequence change(s) between two organisms, species, subspecies, varieties, cultivars and/or strains that may be attributed to a positive selective pressure. One method for determining the presence of an evolutionarily significant change is to apply a $K_A/K_S$-type analytical method, such as to measure a $K_A/K_S$ ratio. Typically, a $K_A/K_S$ ratio at least about 0.75, more preferably at least about 1.0, more preferably at least about 1.25, more preferably at least about 1.5 and most preferably at least about 2.0 indicates the action of positive selection and is considered to be an evolutionarily significant change.

The term "positive evolutionarily significant change" means an evolutionarily significant change in a particular organism, species, subspecies, variety, cultivar or strain that results in an adaptive change that is positive as compared to other related organisms. An example of a positive evolutionarily significant change is a change that has resulted in enhanced yield in crop plants.

The term "resistant" means that an organism exhibits an ability to avoid, or diminish the extent of, a disease condition and/or development of the disease, preferably when compared to non-resistant organisms.

The term "susceptibility" means that an organism fails to avoid, or diminish the extent of, a disease condition and/or development of the disease condition, preferably when compared to an organism that is known to be resistant.

It is understood that resistance and susceptibility vary from individual to individual, and that, for purposes of this invention, these terms also apply to a group of individuals within a species, and comparisons of resistance and susceptibility generally refer to overall, average differences between species, although intra-specific comparisons may be used.

The term "homologous" or "homologue" or "ortholog" is known and well understood in the art and refers to related sequences that share a common ancestor and is determined based on degree of sequence identity. These terms describe the relationship between a gene found in one species, subspecies, variety, cultivar or strain and the corresponding or equivalent gene in another species, subspecies, variety, cultivar or strain. For purposes of this invention homologous sequences are compared. "Homologous sequences" or "homologues" or "orthologs" are thought, believed, or known to be functionally related. A functional relationship may be indicated in any one of a number of ways, including, but not limited to, (a) degree of sequence identity; (b) same or similar biological function. Preferably, both (a) and (b) are indicated. The degree of sequence identity may vary, but is preferably at least 50% (when using standard sequence alignment programs known in the art), more preferably at least 60%, more preferably at least about 75%, more preferably at least about 85%. Homology can be determined using software programs readily available in the art, such as those discussed in *Current Protocols in Molecular Biology* (F. M. Ausubel et al., eds., 1987) Supplement 30, section 7.718, Table 7.71. Preferred alignment programs are MacVector (Oxford Molecular Ltd, Oxford, U.K.) and ALIGN Plus (Scientific and Educational Software, Pennsylvania). Another preferred alignment program is Sequencher (Gene Codes, Ann Arbor, Mich.), using default parameters.

The term "nucleotide change" refers to nucleotide substitution, deletion, and/or insertion, as is well understood in the art.

"Housekeeping genes" is a term well understood in the art and means those genes associated with general cell function, including but not limited to growth, division, stasis, metabolism, and/or death. "Housekeeping" genes generally perform functions found in more than one cell type. In contrast, cell-specific genes generally perform functions in a particular cell type and/or class.

The term "agent", as used herein, means a biological or chemical compound such as a simple or complex organic or inorganic molecule, a peptide, a protein or an oligonucleotide that modulates the function of a polynucleotide or polypeptide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

The term "to modulate function" of a polynucleotide or a polypeptide means that the function of the polynucleotide or polypeptide is altered when compared to not adding an agent. Modulation may occur on any level that affects function. A polynucleotide or polypeptide function may be direct or indirect, and measured directly or indirectly.

A "function of a polynucleotide" includes, but is not limited to, replication; translation; expression pattern(s). A polynucleotide function also includes functions associated with a polypeptide encoded within the polynucleotide. For example, an agent which acts on a polynucleotide and affects protein expression, conformation, folding (or other physical characteristics), binding to other moieties (such as ligands), activity (or other functional characteristics), regulation and/or other aspects of protein structure or function is considered to have modulated polynucleotide function.

A "function of a polypeptide" includes, but is not limited to, conformation, folding (or other physical characteristics), binding to other moieties (such as ligands), activity (or other functional characteristics), and/or other aspects of protein structure or functions. For example, an agent that acts on a polypeptide and affects its conformation, folding (or other physical characteristics), binding to other moieties (such as ligands), activity (or other functional characteristics), and/or other aspects of protein structure or functions is considered to have modulated polypeptide function. The ways that an effective agent can act to modulate the function of a polypeptide include, but are not limited to 1) changing the conformation, folding or other physical characteristics; 2) changing the binding strength to its natural ligand or changing the specificity of binding to ligands; and 3) altering the activity of the polypeptide.

The term "target site" means a location in a polypeptide which can be a single amino acid and/or is a part of, a structural and/or functional motif, e.g., a binding site, a dimerization domain, or a catalytic active site. Target sites may be useful for direct or indirect interaction with an agent, such as a therapeutic agent.

The term "molecular difference" includes any structural and/or functional difference. Methods to detect such differences, as well as examples of such differences, are described herein.

A "functional effect" is a term well known in the art, and means any effect which is exhibited on any level of activity, whether direct or indirect.

The term "ease of harvest" refers to plant characteristics or features that facilitate manual or automated collection of structures or portions (e.g., fruit, leaves, roots) for consumption or other commercial processing.

General Procedures Known in the Art

For the purposes of this invention, the source of the polynucleotide from the domesticated plant or animal or its ancestor can be any suitable source, e.g., genomic sequences or cDNA sequences. Preferably, cDNA sequences are compared. Protein-coding sequences can be obtained from available private, public and/or commercial databases such as those described herein. These databases serve as repositories of the molecular sequence data generated by ongoing research efforts. Alternatively, protein-coding sequences may be obtained from, for example, sequencing of cDNA reverse transcribed from mRNA expressed in cells, or after PCR amplification, according to methods well known in the art. Alternatively, genomic sequences may be used for sequence comparison. Genomic sequences can be obtained from available public, private and/or commercial databases or from a sequencing of commercially available genomic DNA libraries or from genomic DNA, after PCR.

In some embodiments, the cDNA is prepared from mRNA obtained from a tissue at a determined developmental stage, or a tissue obtained after the organism has been subjected to certain environmental conditions. cDNA libraries used for the sequence comparison of the present invention can be constructed using conventional cDNA library construction techniques that are explained fully in the literature of the art. Total mRNAs are used as templates to reverse-transcribe cDNAs. Transcribed cDNAs are subcloned into appropriate vectors to establish a cDNA library. The established cDNA library can be maximized for full-length cDNA contents, although less than full-length cDNAs may be used. Furthermore, the sequence frequency can be normalized according to, for example, Bonaldo et al. (1996) *Genome Research* 6:791–806. cDNA clones randomly selected from the constructed cDNA library can be sequenced using standard automated sequencing techniques. Preferably, full-length cDNA clones are used for sequencing. Either the entire or a large portion of cDNA clones from a cDNA library may be sequenced, although it is also possible to practice some embodiments of the invention by sequencing as little as a single cDNA, or several cDNA clones.

In one preferred embodiment of the present invention, cDNA clones to be sequenced can be pre-selected according to their expression specificity. In order to select cDNAs corresponding to active genes that are specifically expressed, the cDNAs can be subject to subtraction hybridization using mRNAs obtained from other organs, tissues or cells of the same animal. Under certain hybridization conditions with appropriate stringency and concentration, those cDNAs that hybridize with non-tissue specific mRNAs and thus likely represent "housekeeping" genes will be excluded from the cDNA pool. Accordingly, remaining cDNAs to be sequenced are more likely to be associated with tissue-specific functions. For the purpose of subtraction hybridization, non-tissue-specific mRNAs can be obtained from one organ, or preferably from a combination of different organs and cells. The amount of non-tissue-specific mRNAs are maximized to saturate the tissue-specific cDNAs.

Alternatively, information from online databases can be used to select or give priority to cDNAs that are more likely to be associated with specific functions. For example, the ancestral cDNA candidates for sequencing can be selected by PCR using primers designed from candidate domesticated organism cDNA sequences. Candidate domesticated organism cDNA sequences are, for example, those that are only found in a specific tissue, such as skeletal muscle, or that correspond to genes likely to be important in the specific function. Such tissue-specific cDNA sequences may be obtained by searching online sequence databases in which information with respect to the expression profile and/or biological activity for cDNA sequences may be specified.

Sequences of ancestral homologue(s) to a known domesticated organism's gene may be obtained using methods standard in the art, such as PCR methods (using, for example, GeneAmp PCR System 9700 thermocyclers (Applied Biosystems, Inc.)). For example, ancestral cDNA candidates for sequencing can be selected by PCR using primers designed from candidate domesticated organism cDNA sequences. For PCR, primers may be made from the domesticated organism's sequences using standard methods in the art, including publicly available primer design programs such as PRIMER® (Whitehead Institute). The ancestral sequence amplified may then be sequenced using standard methods and equipment in the art, such as automated sequencers (Applied Biosystems, Inc.).

GENERAL METHODS OF THE INVENTION

The general method of the invention is as follows. Briefly, nucleotide sequences are obtained from a domesticated organism and a wild ancestor. The domesticated organism's and ancestor's nucleotide sequences are compared to one another to identify sequences that are homologous. The homologous sequences are analyzed to identify those that have nucleic acid sequence differences between the domesticated organism and ancestor. Then molecular evolution analysis is conducted to evaluate quantitatively and qualitatively the evolutionary significance of the differences. For genes that have been positively selected, outgroup analysis can be done to identify those genes that have been positively selected in the domesticated organism (as opposed to the ancestor). Next, the sequence is characterized in terms of molecular/genetic identity and biological function. Finally, the information can be used to identify agents that can modulate the biological function of the polypeptide encoded by the gene.

The general methods of the invention entail comparing protein-coding nucleotide sequences of ancestral and domesticated organisms. Bioinformatics is applied to the comparison and sequences are selected that contain a nucleotide change or changes that is/are evolutionarily significant change(s). The invention enables the identification of genes that have evolved to confer some evolutionary advantage and the identification of the specific evolved changes.

Protein-coding sequences of a domesticated organism and its ancestor are compared to identify homologous sequences. Any appropriate mechanism for completing this comparison is contemplated by this invention. Alignment may be performed manually or by software (examples of suitable alignment programs are known in the art). Preferably, protein-coding sequences from an ancestor are compared to the domesticated species sequences via database searches, e.g., BLAST searches. The high scoring "hits," i.e., sequences that show a significant similarity after BLAST analysis, will be retrieved and analyzed. Sequences showing a significant similarity can be those having at least about 60%, at least about 75%, at least about 80%, at least about 85%, or at least about 90% sequence identity. Preferably, sequences showing greater than about 80% identity are further analyzed. The homologous sequences identified via database searching can be aligned in their entirety using sequence alignment methods and programs that are known and available in the art, such as the commonly used simple alignment program CLUSTAL V by Higgins et al. (1992) *CABIOS* 8:189–191.

Alternatively, the sequencing and homology comparison of protein-coding sequences between the domesticated organism and its ancestor may be performed simultaneously by using the newly developed sequencing chip technology. See, for example, Rava et al. U.S. Pat. No. 5,545,531.

The aligned protein-coding sequences of domesticated organism and ancestor are analyzed to identify nucleotide sequence differences at particular sites. Again, any suitable method for achieving this analysis is contemplated by this invention. If there are no nucleotide sequence differences, the ancestor protein coding sequence is not usually further analyzed. The detected sequence changes are generally, and preferably, initially checked for accuracy. Preferably, the initial checking comprises performing one or more of the following steps, any and all of which are known in the art: (a) finding the points where there are changes between the ancestral and domesticated organism sequences; (b) checking the sequence fluorogram (chromatogram) to determine if the bases that appear unique to the ancestor or domesticated organism correspond to strong, clear signals specific for the called base; (c) checking the domesticated organism hits to see if there is more than one domesticated organism sequence that corresponds to a sequence change. Multiple domesticated organism sequence entries for the same gene that have the same nucleotide at a position where there is a different nucleotide in an ancestor sequence provides independent support that the domesticated sequence is accurate, and that the change is significant. Such changes are examined using database information and the genetic code to determine whether these nucleotide sequence changes result in a change in the amino acid sequence of the encoded protein. As the definition of "nucleotide change" makes clear, the present invention encompasses at least one nucleotide change, either a substitution, a deletion or an insertion, in a protein-coding polynucleotide sequence of a domesticated organism as compared to a corresponding sequence from the ancestor. Preferably, the change is a nucleotide substitution. More preferably, more than one substitution is present in the identified sequence and is subjected to molecular evolution analysis.

Any of several different molecular evolution analyses or $K_A/K_S$-type methods can be employed to evaluate quantitatively and qualitatively the evolutionary significance of the identified nucleotide changes between domesticated species gene sequences and those of corresponding ancestors. Kreitman and Akashi (1995) *Annu. Rev. Ecol. Syst.* 26:403–422; Li, *Molecular Evolution*, Sinauer Associates, Sunderland, Mass., 1997. For example, positive selection on proteins (i.e., molecular-level adaptive evolution) can be detected in protein-coding genes by pairwise comparisons of the ratios of nonsynonymous nucleotide substitutions per nonsynonymous site ($K_A$) to synonymous substitutions per synonymous site ($K_S$) (Li et al., 1985; Li, 1993). Any comparison of $K_A$ and $K_S$ may be used, although it is particularly convenient and most effective to compare these two variables as a ratio. Sequences are identified by exhibiting a statistically significant difference between $K_A$ and $K_S$ using standard statistical methods.

Preferably, the $K_A/K_S$ analysis by Li et al. is used to carry out the present invention, although other analysis programs that can detect positively selected genes between species can also be used. Li et al. (1985) *Mol. Biol. Evol.* 2:150–174; Li (1993); see also *J. Mol. Evol.* 36:96–99; Messier and Stewart (1997) *Nature* 385:151–154; Nei (1987) *Molecular Evolutionary Genetics* (New York, Columbia University Press). The $K_A/K_S$ method, which comprises a comparison of the rate of non-synonymous substitutions per non-synonymous site with the rate of synonymous substitutions per synonymous site between homologous protein-coding region of genes in terms of a ratio, is used to identify sequence substitutions that may be driven by adaptive selections as opposed to neutral selections during evolution. A synonymous ("silent") substitution is one that, owing to the degeneracy of the genetic code, makes no change to the amino acid sequence encoded; a non-synonymous substitution results in an amino acid replacement. The extent of each type of change can be estimated as $K_A$ and $K_S$, respectively, the numbers of synonymous substitutions per synonymous site and non-synonymous substitutions per non-synonymous site. Calculations of $K_A/K_S$ may be performed manually or by using software. An example of a suitable program is MEGA (Molecular Genetics Institute, Pennsylvania State University).

For the purpose of estimating $K_A$ and $K_S$, either complete or partial protein-coding sequences are used to calculate total numbers of synonymous and non-synonymous substitutions, as well as non-synonymous and synonymous sites. The length of the polynucleotide sequence analyzed can be any appropriate length. Preferably, the entire coding sequence is compared, in order to determine any and all significant changes. Publicly available computer programs, such as Li93 (Li (1993) *J. Mol. Evol.* 36:96–99) or INA, can be used to calculate the $K_A$ and $K_S$ values for all pairwise comparisons. This analysis can be further adapted to examine sequences in a "sliding window" fashion such that small numbers of important changes are not masked by the whole sequence. "Sliding window" refers to examination of consecutive, overlapping subsections of the gene (the subsections can be of any length).

The comparison of non-synonymous and synonymous substitution rates is represented by the $K_A/K_S$ ratio. $K_A/K_S$ has been shown to be a reflection of the degree to which adaptive evolution has been at work in the sequence under study. Full length or partial segments of a coding sequence can be used for the $K_A/K_S$ analysis. The higher the $K_A/K_S$ ratio, the more likely that a sequence has undergone adaptive evolution and the non-synonymous substitutions are evolutionarily significant. See, for example, Messier and Stewart (1997). Preferably, the $K_A/K_S$ ratio is at least about 0.75, more preferably at least about 1.0, more preferably at least about 1.25, more preferably at least about 1.50, or more preferably at least about 2.00. Preferably, statistical analysis is performed on all elevated $K_A/K_S$ ratios, including, but not limited to, standard methods such as Student's t-test and likelihood ratio tests described by Yang (1998) *Mol. Biol. Evol.* 37:441–456.

For a pairwise comparison of homologous sequences, $K_A/K_S$ ratios significantly greater than unity strongly suggest that positive selection has fixed greater numbers of amino acid replacements than can be expected as a result of chance alone, and is in contrast to the commonly observed pattern in which the ratio is less than or equal to one. Nei (1987); Hughes and Hei (1988) *Nature* 335:167–170; Messier and Stewart (1994) *Current Biol.* 4:911–913; Kreitman and Akashi (1995) *Ann. Rev. Ecol. Syst.* 26:403–422; Messier and Stewart (1997). Ratios less than one generally signify the role of negative, or purifying selection: there is strong pressure on the primary structure of functional, effective proteins to remain unchanged.

All methods for calculating $K_A/K_S$ ratios are based on a pairwise comparison of the number of nonsynonymous substitutions per nonsynonymous site to the number of synonymous substitutions per synonymous site for the protein-coding regions of homologous genes from the ancestral and domesticated organisms. Each method implements different corrections for estimating "multiple hits" (i.e., more than one nucleotide substitution at the same site). Each method also uses different models for how DNA sequences change over evolutionary time. Thus, preferably, a combination of results from different algorithms is used to increase the level of sensitivity for detection of positively-selected genes and confidence in the result.

Preferably, $K_A/K_S$ ratios should be calculated for orthologous gene pairs, as opposed to paralogous gene pairs (i.e., a gene which results from speciation, as opposed to a gene that is the result of gene duplication) Messier and Stewart (1997). This distinction may be made by performing additional comparisons with other ancestors, which allows for phylogenetic tree-building. Orthologous genes when used in tree-building will yield the known "species tree", i.e., will produce a tree that recovers the known biological tree. In contrast, paralogous genes will yield trees which will violate the known biological tree.

It is understood that the methods described herein could lead to the identification of ancestral or domesticated organism polynucleotide sequences that are functionally related to the protein-coding sequences. Such sequences may include, but are not limited to, non-coding sequences or coding sequences that do not encode proteins. These related sequences can be, for example, physically adjacent to the protein-coding sequences in the genome, such as introns or 5'- and 3'-flanking sequences (including control elements such as promoters and enhancers). These related sequences may be obtained via searching available public, private and/or commercial genome databases or, alternatively, by screening and sequencing the organism's genomic library with a protein-coding sequence as probe. Methods and techniques for obtaining non-coding sequences using related coding sequence are well known for one skilled in the art.

The evolutionarily significant nucleotide changes, which are detected by molecular evolution analysis such as the $K_A/K_S$ analysis, can be further assessed for their unique occurrence in the domesticated organism or the extent to which these changes are unique in the domesticated organism. For example, the identified changes in the domesticated gene can be tested for presence/absence in other sequences of related species, subspecies or other organisms having a common ancestor with the domesticated organism. This comparison ("outgroup analysis") permits the determination of whether the positively selected gene is positively selected for the domesticated organism at issue (as opposed to the ancestor).

The sequences with at least one evolutionarily significant change between a domesticated organism and its ancestor can be used as primers for PCR analysis of other ancestor protein-coding sequences, and resulting polynucleotides are sequenced to see whether the same change is present in other ancestors. These comparisons allow further discrimination as to whether the adaptive evolutionary changes are unique to the domesticated lineage as compared to other ancestors or whether the adaptive change is unique to the ancestor as compared to the domesticated species and other ancestors. A nucleotide change that is detected in domesticated organism but not other ancestors more likely represents an adaptive evolutionary change in the domesticated organism. Alternatively, a nucleotide change that is detected in an ancestor that is not detected in the domesticated organism or other ancestors likely represents an ancestor adaptive evolutionary change. Other ancestors used for comparison can be selected based on their phylogenetic relationships with the domesticated organism. Statistical significance of such comparisons may be determined using established available programs, e.g., t-test as used by Messier and Stewart (1997) *Nature* 385:151–154. Those genes showing statistically high $K_A/K_S$ ratios are very likely to have undergone adaptive evolution.

Sequences with significant changes can be used as probes in genomes from different domesticated populations to see whether the sequence changes are shared by more than one domesticated population. Gene sequences from different domesticated populations can be obtained from databases or, alternatively, from direct sequencing of PCR-amplified DNA from a number of unrelated, diverse domesticated populations. The presence of the identified changes in different domesticated populations would further indicate the evolutionary significance of the changes.

Sequences with significant changes between species can be further characterized in terms of their molecular/genetic identities and biological functions, using methods and techniques known to those of ordinary skill in the art. For example, the sequences can be located genetically and physically within the organism's genome using publicly available bio-informatics programs. The newly identified significant changes within the nucleotide sequence may suggest a potential role of the gene in the organism's evolution and a potential association with unique, enhanced or altered functional capabilities. The putative gene with the identified sequences may be further characterized by, for example, homologue searching. Shared homology of the putative gene with a known gene may indicate a similar biological role or function. Another exemplary method of characterizing a putative gene sequence is on the basis of known sequence motifs. Certain sequence patterns are known to code for regions of proteins having specific biological characteristics such as signal sequences, DNA binding domains, or transmembrane domains.

The identified sequences with significant changes can also be further evaluated by looking at where the gene is expressed in terms of tissue- or cell type-specificity. For example, the identified coding sequences can be used as probes to perform in situ mRNA hybridization that will reveal the expression patterns of the sequences. Genes that are expressed in certain tissues may be better candidates as being associated with important functions associated with that tissue, for example skeletal muscle tissue. The timing of the gene expression during each stage of development of a species member can also be determined.

As another exemplary method of sequence characterization, the functional roles of the identified nucleotide sequences with significant changes can be assessed by conducting functional assays for different alleles of an identified gene in the transfected domesticated organism, e.g., in the transgenic plant or animal.

As another exemplary method of sequence characterization, the use of computer programs allows modeling and visualizing the three-dimensional structure of the homologous proteins from domesticated organism and ancestor. Specific, exact knowledge of which amino acids have been replaced in the ancestor protein(s) allows detection of structural changes that may be associated with functional differences. Thus, use of modeling techniques is closely associated with identification of finctional roles discussed in the previous paragraph. The use of individual or combinations of these techniques constitutes part of the present invention.

A domesticated organism's gene identified by the subject method can be used to identify homologous genes in other species that share a common ancestor. For example, corn, rice, wheat, millet and sorghum share a common ancestor, and genes identified in corn can lead directly to homologous genes in these other grasses. Likewise, tomatoes and potatoes share a common ancestor, and genes identified in tomatoes by the subject method are expected to have homologues in potatoes.

The sequences identified by the methods described herein can be used to identify agents that are usefull in modulating domesticated organism-unique, enhanced or altered functional capabilities and/or correcting defects in these capabilities using these sequences. These methods employ, for example, screening techniques known in the art, such as in vitro systems, cell-based expression systems and transgenic animals and plants. The approach provided by the present invention not only identifies rapidly evolved genes, but indicates modulations that can be made to the protein that may not be too toxic because they exist in another species.

Screening methods

The present invention also provides screening methods using the polynucleotides and polypeptides identified and characterized using the above-described methods. These screening methods are useful for identifying agents which may modulate the function(s) of the polynucleotides or polypeptides in a manner that would be useful for enhancing or diminishing a characteristic in a domesticated organism. Generally, the methods entail contacting at least one agent to be tested with either a transgenic organism or cell that has been transfected with a polynucleotide sequence identified by the methods described above, or a preparation of the polypeptide encoded by such polynucleotide sequence, wherein an agent is identified by its ability to modulate function of either the polynucleotide sequence or the polypeptide. For example, an agent can be a compound that is applied or contacted with a domesticated plant or animal to induce expression of the identified gene at a desired time. Specifically in regard to plants, an agent could be used to induce flowering at an appropriate time.

As used herein, the term "agent" means a biological or chemical compound such as a simple or complex organic or inorganic molecule, a peptide, a protein or an oligonucleotide. A vast array of compounds can be synthesized, for example oligomers, such as oligopeptides and oligonucleotides, and synthetic organic and inorganic compounds based on various core structures, and these are also included in the term "agent". In addition, various natural sources can provide compounds for screening, such as plant or animal extracts, and the like. Compounds can be tested singly or in combination with one another.

To "modulate function" of a polynucleotide or a polypeptide means that the finction of the polynucleotide or polypeptide is altered when compared to not adding an agent. Modulation may occur on any level that affects function. A polynucleotide or polypeptide function may be direct or indirect, and measured directly or indirectly. A "function" of a polynucleotide includes, but is not limited to, replication, translation, and expression pattern(s). A polynucleotide function also includes functions associated with a polypeptide encoded within the polynucleotide. For example, an agent which acts on a polynucleotide and affects protein expression, conformation, folding (or other physical characteristics), binding to other moieties (such as ligands), activity (or other functional characteristics), regulation and/ or other aspects of protein structure or function is considered to have modulated polynucleotide function. The ways that an effective agent can act to modulate the expression of a polynucleotide include, but are not limited to 1) modifying binding of a transcription factor to a transcription factor responsive element in the polynucleotide; 2) modifying the interaction between two transcription factors necessary for expression of the polynucleotide; 3) altering the ability of a transcription factor necessary for expression of the polynucleotide to enter the nucleus; 4) inhibiting the activation of a transcription factor involved in transcription of the polynucleotide; 5) modifying a cell-surface receptor which normally interacts with a ligand and whose binding of the ligand results in expression of the polynucleotide; 6) inhibiting the inactivation of a component of the signal transduction cascade that leads to expression of the polynucleotide; and 7) enhancing the activation of a transcription factor involved in transcription of the polynucleotide.

A "function" of a polypeptide includes, but is not limited to, conformation, folding (or other physical characteristics), binding to other moieties (such as ligands), activity (or other functional characteristics), and/or other aspects of protein structure or functions. For example, an agent that acts on a polypeptide and affects its conformation, folding (or other physical characteristics), binding to other moieties (such as ligands), activity (or other functional characteristics), and/or other aspects of protein structure or functions is considered to have modulated polypeptide function. The ways that an effective agent can act to modulate the function of a polypeptide include, but are not limited to 1) changing the conformation, folding or other physical characteristics; 2) changing the binding strength to its natural ligand or changing the specificity of binding to ligands; and 3) altering the activity of the polypeptide.

Generally, the choice of agents to be screened is governed by several parameters, such as the particular polynucleotide or polypeptide target, its perceived function, its three-dimensional structure (if known or surmised), and other aspects of rational drug design. Techniques of combinatorial chemistry can also be used to generate numerous permutations of candidates. Those of skill in the art can devise and/or obtain suitable agents for testing.

The in vivo screening assays described herein may have several advantages over conventional drug screening assays: 1) if an agent must enter a cell to achieve a desired therapeutic effect, an in vivo assay can give an indication as to whether the agent can enter a cell; 2) an in vivo screening assay can identify agents that, in the state in which they are added to the assay system are ineffective to elicit at least one characteristic which is associated with modulation of polynucleotide or polypeptide function, but that are modified by cellular components once inside a cell in such a way that they become effective agents; 3) most importantly, an in vivo assay system allows identification of agents affecting any component of a pathway that ultimately results in characteristics that are associated with polynucleotide or polypeptide function.

In general, screening can be performed by adding an agent to a sample of appropriate cells which have been transfected with a polynucleotide identified using the methods of the present invention, and monitoring the effect, i.e., modulation of a function of the polynucleotide or the polypeptide encoded within the polynucleotide. The experiment preferably includes a control sample which does not receive the candidate agent. The treated and untreated cells are then compared by any suitable phenotypic criteria, including but not limited to microscopic analysis, viability testing, ability to replicate, histological examination, the level of a particular RNA or polypeptide associated with the cells, the level of enzymatic activity expressed by the cells or cell lysates, the interactions of the cells when exposed to infectious agents, and the ability of the cells to interact with other cells or compounds. Differences between treated and untreated cells indicate effects attributable to the candidate agent. Optimally, the agent has a greater effect on experimental cells than on control cells. Appropriate host cells include, but are not limited to, eukaryotic cells, preferably mammalian cells. The choice of cell will at least partially depend on the nature of the assay contemplated.

To test for agents that upregulate the expression of a polynucleotide, a suitable host cell transfected with a polynucleotide of interest, such that the polynucleotide is expressed (as used herein, expression includes transcription and/or translation) is contacted with an agent to be tested. An agent would be tested for its ability to result in increased expression of mRNA and/or polypeptide. Methods of making vectors and transfection are well known in the art. "Transfection" encompasses any method of introducing the exogenous sequence, including, for example, lipofection, transduction, infection or electroporation. The exogenous polynucleotide may be maintained as a non-integrated vector (such as a plasmid) or may be integrated into the host genome.

To identify agents that specifically activate transcription, transcription regulatory regions could be linked to a reporter gene and the construct added to an appropriate host cell. As used herein, the term "reporter gene" means a gene that encodes a gene product that can be identified (i.e., a reporter protein). Reporter genes include, but are not limited to, alkaline phosphatase, chloramphenicol acetyltransferase, β-galactosidase, luciferase and green fluorescence protein (GFP). Identification methods for the products of reporter genes include, but are not limited to, enzymatic assays and fluorimetric assays. Reporter genes and assays to detect their products are well known in the art and are described, for example in Ausubel et al. (1987) and periodic updates. Reporter genes, reporter gene assays, and reagent kits are also readily available from commercial sources. Examples of appropriate cells include, but are not limited to, fungal, yeast, mammalian, and other eukaryotic cells. A practitioner of ordinary skill will be well acquainted with techniques for transfecting eukaryotic cells, including the preparation of a suitable vector, such as a viral vector; conveying the vector into the cell, such as by electroporation; and selecting cells that have been transformed, such as by using a reporter or drug sensitivity element. The effect of an agent on transcription from the regulatory region in these constructs would be assessed through the activity of the reporter gene product.

Besides the increase in expression under conditions in which it is normally repressed mentioned above, expression could be decreased when it would normally be expressed. An agent could accomplish this through a decrease in transcription rate and the reporter gene system described above would be a means to assay for this. The host cells to assess such agents would need to be permissive for expression.

Cells transcribing mRNA (from the polynucleotide of interest) could be used to identify agents that specifically modulate the half-life of mRNA and/or the translation of mRNA. Such cells would also be used to assess the effect of an agent on the processing and/or post-translational modification of the polypeptide. An agent could modulate the amount of polypeptide in a cell by modifying the turn-over (i.e., increase or decrease the half-life) of the polypeptide. The specificity of the agent with regard to the mRNA and polypeptide would be determined by examining the products in the absence of the agent and by examining the products of unrelated mRNAs and polypeptides. Methods to examine mRNA half-life, protein processing, and protein turn-over are well know to those skilled in the art.

In vivo screening methods could also be useful in the identification of agents that modulate polypeptide function through the interaction with the polypeptide directly. Such agents could block normal polypeptide-ligand interactions, if any, or could enhance or stabilize such interactions. Such agents could also alter a conformation of the polypeptide. The effect of the agent could be determined using immunoprecipitation reactions. Appropriate antibodies would be used to precipitate the polypeptide and any protein tightly associated with it. By comparing the polypeptides immunoprecipitated from treated cells and from untreated cells, an agent could be identified that would augment or inhibit polypeptide-ligand interactions, if any. Polypeptide-ligand interactions could also be assessed using cross-linking reagents that convert a close, but noncovalent interaction between polypeptides into a covalent interaction. Techniques to examine protein—protein interactions are well known to those skilled in the art. Techniques to assess protein conformation are also well known to those skilled in the art.

It is also understood that screening methods can involve in vitro methods, such as cell-free transcription or translation systems. In those systems, transcription or translation is allowed to occur, and an agent is tested for its ability to modulate function. For an assay that determines whether an agent modulates the translation of mRNA or a polynucleotide, an in vitro transcription/translation system may be used. These systems are available commercially and provide an in vitro means to produce mRNA corresponding to a polynucleotide sequence of interest After mRNA is made, it can be translated in vitro and the translation products compared. Comparison of translation products between an in vitro expression system that does not contain any agent (negative control) with an in vitro expression system that does contain an agent indicates whether the agent is affecting translation. Comparison of translation products between control and test polynucleotides indicates whether the agent, if acting on this level, is selectively affecting translation (as opposed to affecting translation in a general, non-selective or non-specific fashion). The modulation of polypeptide function can be accomplished in many ways including, but not limited to, the in vivo and in vitro assays listed above as well as in in vitro assays using protein preparations. Polypeptides can be extracted and/or purified from natural or recombinant sources to create protein preparations. An agent can be added to a sample of a protein preparation and the effect monitored; that is whether and how the agent acts on a polypeptide and affects its conformation, folding (or other physical characteristics), binding to other moieties (such as ligands), activity (or other functional characteristics), and/or other aspects of protein structure or functions is considered to have modulated polypeptide function.

In an example for an assay for an agent that binds to a polypeptide encoded by a polynucleotide identified by the methods described herein, a polypeptide is first recombinantly expressed in a prokaryotic or eukaryotic expression system as a native or as a fusion protein in which a polypeptide (encoded by a polynucleotide identified as described above) is conjugated with a well-characterized epitope or protein. Recombinant polypeptide is then purified by, for instance, immunoprecipitation using appropriate antibodies or anti-epitope antibodies or by binding to immobilized ligand of the conjugate. An affinity column made of polypeptide or fusion protein is then used to screen a mixture of compounds which have been appropriately labeled. Suitable labels include, but are not limited to fluorochromes, radioisotopes, enzymes and chemiluminescent compounds. The unbound and bound compounds can be separated by washes using various conditions (e.g. high salt, detergent) that are routinely employed by those skilled in the art. Non-specific binding to the affinity column can be minimized by pre-clearing the compound mixture using an affinity column containing merely the conjugate or the epitope. Similar methods can be used for screening for an agent(s) that competes for binding to polypeptides. In addition to affinity chromatography, there are other techniques such as measuring the change of melting temperature or the fluorescence anisotropy of a protein which will change upon binding another molecule. For example, a BIAcore assay using a sensor chip (supplied by Pharmacia Biosensor, Stitt et al. (1995) *Cell* 80: 661–670) that is covalently coupled to polypeptide may be performed to determine the binding activity of different agents.

It is also understood that the in vitro screening methods of this invention include structural, or rational, drug design, in which the amino acid sequence, three-dimensional atomic structure or other property (or properties) of a polypeptide provides a basis for designing an agent which is expected to bind to a polypeptide. Generally, the design and/or choice of agents in this context is governed by several parameters, such as side-by-side comparison of the structures of a domesticated organism's and homologous ancestral polypeptides, the perceived function of the polypeptide target, its three-dimensional structure (if known or surmised), and other aspects of rational drug design. Techniques of combinatorial chemistry can also be used to generate numerous permutations of candidate agents.

Also contemplated in screening methods of the invention are transgenic animal and plant systems, which are known in the art.

The screening methods described above represent primary screens, designed to detect any agent that may exhibit activity that modulates the function of a polynucleotide or polypeptide. The skilled artisan will recognize that secondary tests will likely be necessary in order to evaluate an agent further. For example, a secondary screen may comprise testing the agent(s) in an infectivity assay using mice and other animal models (such as rat), which are known in the art or the domesticated plant or animal itself. In addition, a cytotoxicity assay would be performed as a further corroboration that an agent which tested positive in a primary screen would be suitable for use in living organisms. Any assay for cytotoxicity would be suitable for this purpose, including, for example the MTT assay (Promega).

The invention also includes agents identified by the screening methods described herein.

The following examples are provided to further assist those of ordinary skill in the art. Such examples are intended to be illustrative and therefore should not be regarded as limiting the invention. A number of exemplary modifications and variations are described in this application and others will become apparent to those of skill in this art. Such variations are considered to fall within the scope of the invention as described and claimed herein.

EXAMPLES

Example 1 cDNA Library Construction

A domesticated plant or animal cDNA library is constructed using an appropriate tissue from the plant or animal. A person of ordinary skill in the art would know the appropriate tissue to analyze according to the trait of interest. Alternately, the whole organism may be used. For example, 1 day old plant seedlings are known to express most of the plant's genes.

Total RNA is extracted from the tissue (RNeasy kit, Quiagen; RNAse-free Rapid Total RNA kit, 5 Prime—3 Prime, Inc.) and the integrity and purity of the RNA are determined according to conventional molecular cloning methods. Poly A+ RNA is isolated (Mini-Oligo(dT) Cellulose Spin Columns, 5 Prime—3 Prime, Inc.) and used as template for the reverse-transcription of cDNA with oligo (dT) as a primer. The synthesized cDNA is treated and modified for cloning using commercially available kits. Recombinants are then packaged and propagated in a host cell line. Portions of the packaging mixes are amplified and the remainder retained prior to amplification. The library can be normalized and the numbers of independent recombinants in the library is determined.

Example 2

Sequence Comparison

Suitable primers based on a candidate domesticated organism gene are prepared and used for PCR amplification of ancestor cDNA either from a cDNA library or from cDNA prepared from mRNA. Selected ancestor cDNA clones from the cDNA library are sequenced using an automated sequencer, such as an ABI 377. Commonly used primers on the cloning vector such as the M13 Universal and Reverse primers are used to carry out the sequencing. For inserts that are not completely sequenced by end sequencing, dye-labeled terminators or custom primers can be used to fill in remaining gaps.

The detected sequence differences are initially checked for accuracy, for example by finding the points where there are differences between the domesticated and ancestor sequences; checking the sequence fluorogram (chromatogram) to determine if the bases that appear unique to the domesticated organism correspond to strong, clear signals specific for the called base; checking the domesticated organism's hits to see if there is more than one sequence that corresponds to a sequence change; and other methods known in the art, as needed. Multiple domesticated organism sequence entries for the same gene that have the same nucleotide at a position where there is a different ancestor nucleotide provides independent support that the domesticated sequence is accurate, and that the domesticated/ancestor difference is real. Such changes are examined using public or commercial database information and the genetic code to determine whether these DNA sequence changes result in a change in the amino acid sequence of the encoded protein. The sequences can also be examined by direct sequencing of the encoded protein.

Example 3

Molecular Evolution Analysis

The domesticated plant or animal and wild ancestor sequences under comparison are subjected to $K_A/K_S$ analysis. In this analysis, publicly or commercially available computer programs, such as Li 93 and INA, are used to determine the number of non-synonymous changes per site ($K_A$) divided by the number of synonymous changes per site ($K_S$) for each sequence under study as described above. Full-length coding regions or partial segments of a coding region can be used. The higher the $K_A/K_S$ ratio, the more likely that a sequence has undergone adaptive evolution. Statistical significance of $K_A/K_S$ values is determined using established statistic methods and available programs such as the t-test.

To further lend support to the significance of a high $K_A/K_S$ ratio, the domesticated sequence under study can be compared to other evolutionarily proximate species. These comparisons allow further discrimination as to whether the adaptive evolutionary changes are unique to the domesticated plant or animal lineage compared to other closely related species. The sequences can also be examined by direct sequencing of the gene of interest from representatives of several diverse domesticated populations to assess to what degree the sequence is conserved in the domesticated plant or animal.

Example 4 cDNA Library Construction

A teosinte cDNA library is constructed using whole teosinte 1 day old seedlings, or other appropriate plant tissues. Total RNA is extracted from the seedling tissue and the integrity and purity of the RNA are determined according to conventional molecular cloning methods. Poly A+ RNA is selected and used as template for the reverse-transcription of cDNA with oligo (dT) as a primer. The synthesized cDNA is treated and modified for cloning using commercially available kits. Recombinants are then packaged and propagated in a host cell line. Portions of the packaging mixes are amplified and the remainder retained prior to amplification. Recombinant DNA is used to transfect *E. coli* host cells, using established methods. The library can be normalized and the numbers of independent recombinants in the library is determined.

Example 5

Sequence Comparison

Randomly selected teosinte seedling cDNA clones from the cDNA library are sequenced using an automated sequencer, such as the ABI 377. Commonly used primers on the cloning vector such as the M13 Universal and Reverse primers are used to carry out the sequencing. For inserts that are not completely sequenced by end sequencing, dye-labeled terminators are used to fill in remaining gaps.

The resulting teosinte sequences are compared to domesticated corn sequences via database searches. Genome databases are publicly or commercially available for a number of species, including corn. Other appropriate corn EST (expressed sequence tag) databases are privately owned and maintained. The high scoring "hits," i.e., sequences that show a significant (e.g., >80%) similarity after homology analysis, are retrieved and analyzed. The two homologous sequences are then aligned using the alignment program CLUSTAL V developed by Higgins et al. Any sequence divergence, including nucleotide substitution, insertion and deletion, can be detected and recorded by the alignment.

The detected sequence differences are initially checked for accuracy by finding the points where there are differences between the teosinte and corn sequences; checking the sequence fluorogram (chromatogram) to determine if the bases that appear unique to corn correspond to strong, clear signals specific for the called base; checking the corn hits to see if there is more than one corn sequence that corresponds to a sequence change; and other methods known in the art as needed. Multiple corn sequence entries for the same gene that have the same nucleotide at a position where there is a different teosinte nucleotide provides independent support that the corn sequence is accurate, and that the teosinte/corn difference is real. Such changes are examined using public/ commercial database information and the genetic code to determine whether these DNA sequence changes result in a change in the amino acid sequence of the encoded protein. The sequences can also be examined by direct sequencing of the encoded protein.

Example 6

Molecular Evolution Analysis

The teosinte and corn sequences under comparison are subjected to $K_A/K_S$ analysis. In this analysis, publicly or commercially available computer programs, such as Li 93 and INA, are used to determine the number of non-synonymous changes per site ($K_A$) divided by the number of synonymous changes per site ($K_S$) for each sequence under study as described above. This ratio, $K_A/K_S$, has been shown to be a reflection of the degree to which adaptive evolution, i.e., positive selection, has been at work in the sequence under study. Typically, full-length coding regions have been used in these comparative analyses. However, partial segments of a coding region can also be used effectively. The higher the $K_A/K_S$ ratio, the more likely that a sequence has undergone adaptive evolution. Statistical significance of $K_A/K_S$ values is determined using established statistic methods and available programs such as the t-test. Those genes showing statistically high $K_A/K_S$ ratios between teosinte and corn genes are very likely to have undergone adaptive evolution.

To further lend support to the significance of a high $K_A/K_S$ ratio, the sequence under study can be compared in other ancestral corn species. These comparisons allow further discrimination as to whether the adaptive evolutionary changes are unique to the domesticated corn lineage compared to other ancestors. The sequences can also be examined by direct sequencing of the gene of interest from representatives of several diverse corn populations to assess to what degree the sequence is conserved in the corn species.

Example 7
Application of $K_A/K_S$ Method to Corn and Teosinte Homologous Sequences Obtained From a Database Comparison of domesticated corn and teosinte sequences available on Genbank revealed at least four homologous genes: waxy, A1*, A1 and globulin. All available sequences for these genes for both corn and teosinte were compared. The $K_A/K_S$ ratios were determined using Li93 and/or INA:

| Gene | Avr. No. Syn. Substitutions | Avr. No. Non-Syn. Substitutions | $K_A K_S$ |
|---|---|---|---|
| Waxy | 4 | 1 | 0.068 |
| A1* | 10 | 3 | 0.011 |
| A1 | 3 | 2 | 0.44–0.89 |
| Globulin | 10 | 7 | 0.42 |

Although it was anticipated that the polymorphism (multiple allelic copies) and/or the polyploidy (more than 2 sets of chromosomes per cell) observed in corn might make a $K_A/K_S$ analysis complex or difficult, it was found that this was not the case.

While the above $K_A/K_S$ values indicate that these genes are not positively selected, this example illustrates that the $K_A/K_S$ method can be applied to corn and its teosinte sequences obtained from a database.

Example 8
Study of Protein Function Using a Transgenic Plant

The functional roles of a positively selected corn gene obtained according to the methods of Examples 4–7 can be assessed by conducting assessments of each allele of the gene in a transgenic corn plant. A transgenic plant can be created using an adaptation of the method described in Peng et al. (1999) *Nature* 400:256–261. Physiological, morphological and/or biochemical examination of the transgenic plant or protein extracts thereof will permit association of each allele with a particular phenotype.

Example 9
Mapping of Positively Selected Genes to OTLs

QTL (quantitative trait locus) analysis has defined chromosomal regions that contain the genes that control several phenotypic traits of interest in maize, including plant height and oil content. By mapping each positively-selected gene identified by this method onto one of the known QTLs, the specific trait controlled by each positively-selected gene can be rapidly and conclusively identified.

Although the foregoing invention has been described in some detail by way of illustration and example for purposes of clarity and understanding, it will be apparent to those of ordinary skill in the art that certain changes and modifications can be practiced. Therefore, the description and examples should not be construed as limiting the scope of the invention, which is delineated by the appended claims.

What is claimed is:

1. A method for identifying a polynucleotide sequence encoding a polypeptide of a domesticated organism, wherein said polypeptide is or is suspected of being associated with a commercially or aesthetically relevant trait that is unique, enhanced or altered in the domesticated organism as compared to a wild ancestor of said domesticated organism, comprising the steps of:
   a) comparing polypeptide-coding nucleotide sequences of said domesticated organism to polypeptide-coding nucleotide sequences of said wild ancestor; and
   b) selecting a polynucleotide sequence in the domesticated organism that contains a nucleotide change as compared to a corresponding sequence in the wild ancestor, wherein said change is evolutionarily significant, whereby the domestic organism's polynucleotide sequence is identified.

2. The method of claim 1 wherein said domesticated organism is a plant selected from the group consisting of corn, rice, tomato, potato and other domesticated plants whose ancestor is known.

3. The method of claim 2 wherein said domesticated plant is corn and said wild ancestor is teosinte.

4. The method of claim 1 wherein said domesticated organism is an animal selected from the group consisting of pigs, cattle, horses, dogs, cats and other domesticated animals whose ancestor is known.

5. The method of claim 1 wherein the protein-coding nucleotide sequences of said domesticated organism correspond to cDNA.

6. The method of claim 1, wherein the nucleotide change is a non-synonymous substitution.

7. The method of claim 6 wherein the evolutionary significance of the nucleotide change is determined according to the non-synonymous substitution rate ($K_A$) of the nucleotide sequence.

8. The method of claim 7, wherein the evolutionary significance of the nucleotide change is determined by the ratio of the non-synonymous substitution rate ($K_A$) to the synonymous rate ($K_S$) of the nucleotide sequence.

9. The method of claim 8, wherein the $K_A/K_S$ ratio is at least about 0.50.

10. The method of claim 9, wherein the $K_A/K_S$ ratio is at least about 0.75.

11. The method of claim 10, wherein the $K_A/K_S$ ratio is at least about 1.00.

12. The method of claim 1, wherein the domesticated organism is a plant and the relevant trait is selected from the group consisting of yield, short day length flowering, protein content, oil content, taste, ease of harvest, disease resistance, drought resistance and other traits of commercial interest.

13. The method of claim 1, wherein the domesticated organism is an animal and the relevant trait is selected from the group consisting of fat content, protein content, milk production, time to maturity, docility, fecundity, disease resistance and other traits of commercial interest.

14. A method of identifying an agent which may modulate a commercially or aesthetically relevant trait in a domesticated organism, said method comprising contacting at least one candidate agent with a cell or transgenic organism that expresses the polynucleotide sequence identified in claim 1, wherein the agent is identified by its ability to modulate function of the polypeptide encoded by the identified polynucleotide sequence.

15. A method for identifying an evolutionarily significant change in a polypeptide-coding polynucleotide sequence of a domesticated organism comprising the steps of:
   a) comparing polypeptide-coding polynucleotide sequences of said domesticated organism to corresponding sequences of a wild ancestor of said domesticated organism; and
   b) selecting a polynucleotide sequence in said domesticated organism that contains a nucleotide change as compared to the corresponding sequence of the wild ancestor, wherein the change is evolutionarily significant and the polynucleotide is associated with a commercially or aesthetically relevant trait in the domesticated organism, whereby the evolutionarily significant change in the polynucleotide is identified.

16. The method of claim 15 wherein said domesticated organism is a plant selected from the group consisting of corn, rice, tomato, potato and other domesticated plants for which the ancestor is known.

17. The method of claim 16 wherein said domesticated plant is corn and said wild ancestor is teosinte.

18. The method of claim 15 wherein said domesticated organism is an animal selected from the group consisting of pigs, cattle, horses, dogs, cats and other domesticated animals for which the ancestor is known.

19. The method of claim 15 wherein the protein-coding nucleotide sequences of said domesticated organism correspond to cDNA.

20. The method of claim 15, wherein the nucleotide change is a non-synonymous substitution.

21. The method of claim 20 wherein the evolutionary significance of the nucleotide change is determined according to the non-synonymous substitution rate ($K_A$) of the nucleotide sequence.

22. The method of claim 21, wherein the evolutionary significance of the nucleotide change is determined by the ratio of the non-synonymous substitution rate ($K_A$) to the synonymous rate ($K_S$) of the nucleotide sequence.

23. The method of claim 22, wherein the $K_A/K_S$ ratio is at least about 0.50.

24. The method of claim 23, wherein the $K_A/K_S$ ratio is at least about 0.75.

25. The method of claim 24, wherein the $K_A/K_S$ ratio is at least about 1.00.

26. The method of claim 15, where the domesticated organism is a plant and the relevant trait is selected from the group consisting of yield, short day length flowering, protein content, oil content, taste, ease of harvest, drought resistance and other traits of commercial interest.

27. The method of claim 15, wherein the domesticated organism is an animal and the relevant trait is selected from the group consisting of fat content, protein content, milk production, time to maturity, docility, fecundity, disease resistance and other traits of commercial interest.

28. A method of identifying an agent which may modulate a commercially or aesthetically relevant trait of a domesticated organism, said method comprising contacting at least one candidate agent with a cell or transgenic organism that expresses the polynucleotide sequence identified in claim 15, wherein the agent is identified by its ability to modulate function of the polypeptide encoded by said polynucleotide.

29. A method for large scale sequence comparison between polypeptide-coding nucleotide sequences of a domesticated organism and polypeptide-coding sequences from a wild ancestor of said domesticated organism, wherein the domesticated organism polypeptide confers or is suspected of conferring a commercially or aesthetically relevant trait that is unique, enhanced or altered in the domesticated organism as compared to the wild ancestor, comprising:
   a) aligning the domesticated organism sequences with corresponding sequences from the wild ancestor according to sequence homology; and
   b) identifying any nucleotide changes within the domesticated organism sequences as compared to the homologous sequences from the wild ancestor.

30. The method of claim 29, wherein the domesticated organism is a plant selected from the group consisting of corn, rice, tomato and other domesticated plants whose ancestors are known.

31. The method of claim 30 wherein said domesticated plant is corn and said wild ancestor is teosinte.

32. The method of claim 29 wherein said domesticated organism is an animal selected from the group consisting of pigs, cattle, horses, dogs, cats and other domesticated animals whose ancestors are known.

33. The method of claim 29 wherein the protein-coding nucleotide sequences of said domesticated species correspond to cDNA.

34. A method for correlating an evolutionarily significant nucleotide change to a commercially or aesthetically relevant trait that is unique, enhanced or altered in a domesticated organism comprising:
   a) identifying a nucleotide sequence according to claim 1; and
   b) analyzing the functional effect of the presence or absence of the identified sequence in the domesticated organism.

* * * * *